(12) United States Patent
Tachikawa et al.

(10) Patent No.: US 7,659,125 B2
(45) Date of Patent: Feb. 9, 2010

(54) LATEX REAGENT FOR ADIPONECTIN ANALYSIS AND METHOD OF ADIPONECTIN ANALYSIS

(75) Inventors: Tetsuya Tachikawa, Tokushima (JP); Suguru Akamatsu, Tokushima (JP); Tokio Sawai, Tokyo (JP); Ayako Nishimura, Tokyo (JP)

(73) Assignee: Mitsubishi Kagaku Latron, Inc., Tokyo (JP)

( * ) Notice: Subject to any disclaimer, the term of this patent is extended or adjusted under 35 U.S.C. 154(b) by 380 days.

(21) Appl. No.: 10/550,324

(22) PCT Filed: Mar. 24, 2004

(86) PCT No.: PCT/JP2004/004083

§ 371 (c)(1),
(2), (4) Date: Sep. 23, 2005

(87) PCT Pub. No.: WO2004/086040

PCT Pub. Date: Oct. 7, 2004

(65) Prior Publication Data

US 2007/0037207 A1      Feb. 15, 2007

(30) Foreign Application Priority Data

Mar. 24, 2003   (JP)   ............................. 2003-080763

(51) Int. Cl.
   *G01N 33/544*   (2006.01)
   *G01N 33/545*   (2006.01)
   *G01N 33/546*   (2006.01)

(52) U.S. Cl. ........................ 436/531; 436/533; 436/534; 436/538; 436/539; 436/541

(58) Field of Classification Search ........................ None
See application file for complete search history.

(56) References Cited

U.S. PATENT DOCUMENTS

| | | | | |
|---|---|---|---|---|
| 4,118,192 | A | 10/1978 | Sawai et al. | .................... 424/12 |
| 6,461,821 | B1 | 10/2002 | Matsuzawa et al. | ........... 435/7.1 |
| 2005/0048565 | A1 | 3/2005 | Tomita et al. | ................. 435/7.1 |

FOREIGN PATENT DOCUMENTS

| | | |
|---|---|---|
| EP | 1 365 022 A1 | 11/2003 |
| JP | 60-111159 | 6/1985 |
| JP | 06 066795 | 3/1994 |
| JP | 2001-4624 A | 1/2001 |
| WO | WO 99/21577 | 5/1999 |
| WO | WO 03/016906 | 2/2003 |

OTHER PUBLICATIONS

Maeda et al., "cDNA Cloning and Expression of a Novel Adipose Specific Collagen-like Factor, apM1 (Adipose Most Abundant Gene Transcript 1)," Biochemical and Biophysical Research Communications, vol. 221, pp. 286-289 (1996).
Maeda, et al., "Analysis of an expression profile of genes in the human adipose tissue," Gene, vol. 190, pp. 227-235 (1997).
Hiroshi Hirose et al., "Kessei adiponectin noudo to insulin teikousei: kenjyojin oyobi 2-gata tonyoubyou kanjya ni okeru kentou," Meeting of the 75th Japanese endocrinology association study, Abstracts, The Japan Endocrine Society, 2002, page 118.
Yasuichi Ohmoto et al., "Adiponectin no ELISA kit ni tuite," Bio Clinica, vol. 17, pp. 156-159 (2002).
Yasuichi Ohmoto et al., "Adiponectin ELISA kit no kaihatsu to kecchu sonzai youshiki no kaiseki," Medical Science Digest, vol. 28, No. 12, pp. 40-43 (2002).
Kumada et al., "Association of Hypoadiponectinemia With Coronary Artery Disease in Men," Arteriosclerosis, Thrombosis, and Vascular Biology, vol. 23, pp. 85-89 (2003).
Ouchi et al., "Reciprocal Association of C-Reactive Protein With Adiponectin in Blood Stream and Adipose Tissue," Circulation, vol. 107, pp. 671-674 (2003).
Nakano et al., "Isolation and Characterization of GBP28, a novel Gelatin-Binding Protein Purified from Human Plasma," Journal of Biochemistry, vol. 120, pp. 803-812 (1996).
Yukio Arita et al.; "Paradoxical Decrease of an Adipose-Specific Protein, Adiponectin, in Obesity"; Biochemical and Biophysical Research Communications 257; pp. 79-83; (1999).
Communication issued on Jan. 21, 2009 from the European Patent Office for corresponding Japanese Patent Application No. JP60-111159.

*Primary Examiner*—Christopher L Chin
(74) *Attorney, Agent, or Firm*—Heslin Rothenberg Farley & Mesiti P.C.

(57) ABSTRACT

A latex reagent for analyzing adiponectin, comprising a suspension of latex particles carrying a substance which specifically binds to adiponectin, is disclosed. Further, a method for analyzing adiponectin, comprising (1) obtaining a biological liquid possibly containing adiponectin, and (2) bringing the biological liquid, while maintaining the state in which the biological liquid is obtained, into contact with a suspension of latex particles carrying a substance which specifically binds to adiponectin, and optically analyzing a degree of latex-particles-agglutination, is disclosed. According to the latex reagent and the method for analyzing adiponectin, a predilution or pretreatment of the biological liquid to be analyzed is not necessary. Further, the analysis can be performed rapidly and conveniently, and facilities therefor are not limited.

5 Claims, 2 Drawing Sheets

F I G. 1
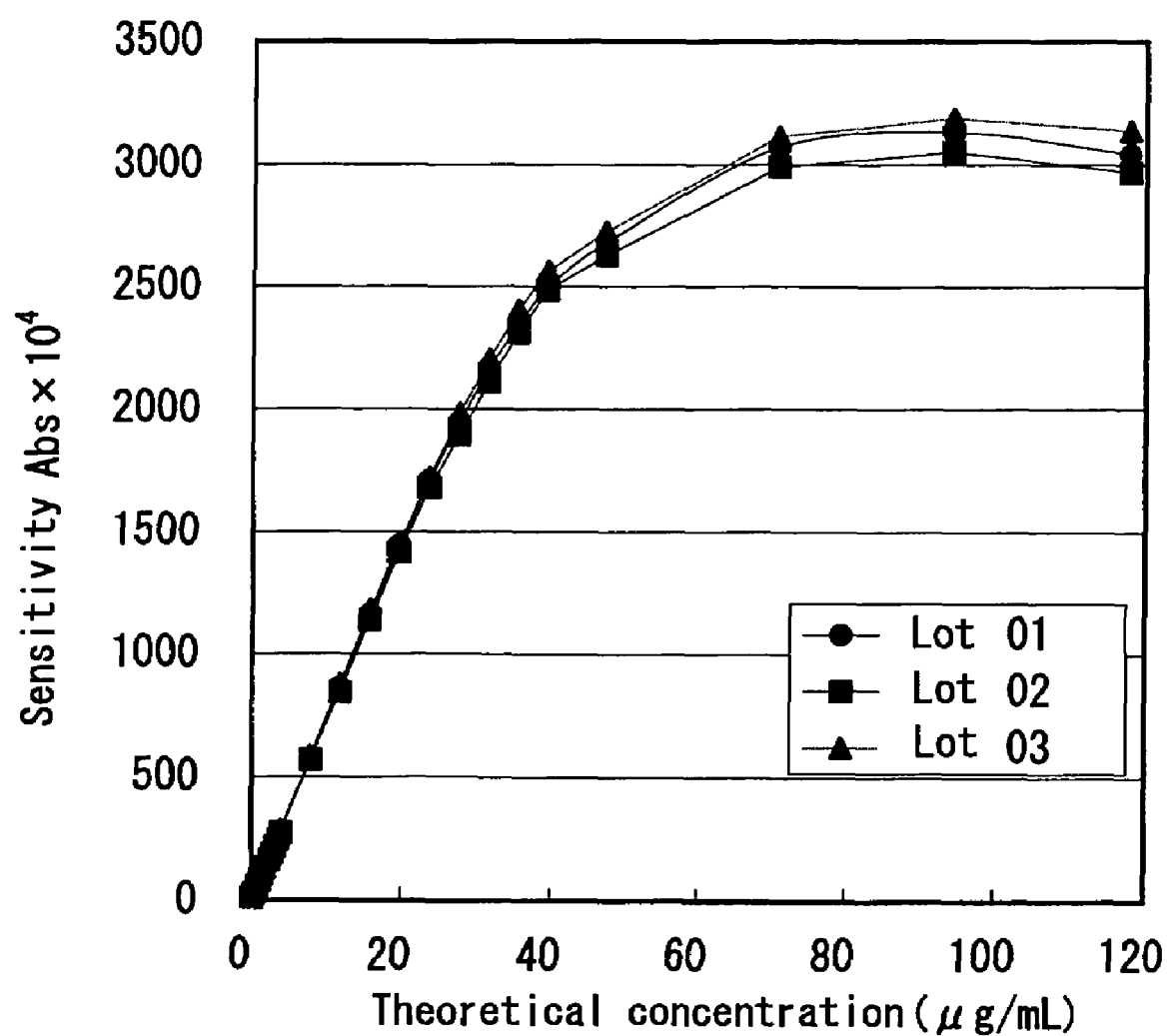

LATEX REAGENT FOR ADIPONECTIN ANALYSIS AND METHOD OF ADIPONECTIN ANALYSIS

CROSS REFERENCE TO RELATED APPLICATIONS

This is the national stage of PCT International application no. PCT/JP2004/004083 filed Mar. 24, 2004 and published in Japanese as WO 2004/086040 on Oct. 7, 2004 which claims the priority of Japanese application no. 2003-080763 filed Mar. 24, 2003, the disclosures of which are hereby incorporated by reference in their entirety.

TECHNICAL FIELD

The present invention relates to a latex reagent for adiponectin analysis and a method of adiponectin analysis. The term "analysis" or "analyzing" as used herein includes a measurement to quantitatively or semi-quantitatively determine an amount of a substance to be analyzed, and a detection to judge a presence or absence of a substance to be analyzed.

BACKGROUND ART

Adiponectin is a secretory protein composed of 244 amino acids, which was identified in 1996 by Matsuzawa (Department of Internal Medicine and Molecular Science, Osaka University; Sumitomo Hospital at present) et al. as a gene product of a gene apM1 (adipose most abundant gene transcript) specifically expressed in adipose tissues (non-patent references 1 and 2). Adiponectin is contained at a high concentration (about 1 μg/mL to several tens of μg/mL) in normal human blood. Although adiponectin is specifically secreted from adipocytes, obese persons show a significantly low concentration thereof in blood, and adiponectin is lowered in patients suffering from coronary diseases or type II diabetes, particularly diabetic macroangiopathy. Adiponectin may be regarded as a molecule involved in insulin resistance and arteriosclerosis. It is important for preventing coronary diseases to measure adiponectin rapidly and accurately.

As a method for measuring adiponectin, an immunological measuring method using an antibody specific to a substance to be analyzed is known (non-patent reference 3). In the immunological measuring method, a radioimmunoassay or an enzyme immunoassay, in which a radioactive substance or an enzyme is used as a label, is utilized to measure an immunocomplex formed by an antigen-antibody reaction (non-patent references 4-7 and patent references 1 and 2). In the radioimmunoassay, facilities for measurement are limited, since a radioactive substance is used. Further, it is generally necessary to dilute a sample to 1/500, and it takes 20 to 24 hours to carry out the measurement. In the enzyme immunoassay, it is generally necessary to pretreat a sample with sodium dodecyl sulfate (SDS) and to predilute a sample to approximately 1/5000, and it takes 2 hours or more to carry out the measurement. As above, the conventional adiponectin measurements need special facilities, complicated procedures, and a long measuring time.

When blood, which reflects a pathosis faithfully, is used as a sample in the above conventional methods, complicated procedures and a long measuring time are needed, and thus, the methods are not suitable for a general purpose assay or a multisample assay. It is desired to develop a measuring reagent for an automatic analysis in which the analysis can be performed rapidly and conveniently, and facilities therefor are not limited.

More particularly, the patent reference 1 discloses an ELISA method for analyzing adiponectin, in which a polyclonal antibody and a monoclonal antibody prepared by using as an immunogen adiponectin expressed in an *Escherichia coil* by genetic recombination techniques are used. The patent reference 1 disclosed that when the ELISA method was used to measure a concentration of adiponectin contained in normal human plasma, without a pretreatment of the plasma sample, the measured value was lower than that previously predicted from a result obtained by Western blotting. As the reason for this, the patent reference 1 discloses a possibility that a site to be recognized by the antibody may be masked, since adiponectin in blood is assembled with other plasma components to form a macromolecule of 290 kDa or more. In the ELISA method disclosed in the patent reference 1, adiponectin in plasma can be measured by diluting the plasma to 1/10 with an SDS-containing buffer, boiling the diluted plasma for 5 minutes, diluting the boiled plasma to approximately 1/5000 as the final concentration, and measuring the 1/5000-diluted plasma. That is, the ELISA method disclosed in the patent reference 1 needs the pretreatment (the heat treatment in the presence of SDS) and the predilution of a sample.

As an ELISA method for analyzing adiponectin which does not need such a pretreatment, the patent reference 2 discloses an ELISA method in which one or more monoclonal antibodies which specifically react with a naturally-occurring adiponectin in blood (particularly, a monoclonal antibody which specifically reacts with a trimeric structure of adiponectin and/or a naturally-occurring adiponectin having a structure in which the trimers are further assembled) is used. According to the disclosure in the patent reference 2, it is known that adiponectin in blood forms a structure in which 4 or 6 trimers composed of 3 monomers are assembled (non-patent reference 8), and the pretreatment of a sample is not necessary in the ELISA method disclosed in the patent reference 2, since one or more monoclonal antibodies specific to a naturally-occurring adiponectin are used. However, the predilution of a sample is an essential step in the ELISA method disclosed in the patent reference 2. As an assay, the patent reference 2 exemplifies, for example, a solid phase method, a competitive method, an agglutination method, a turbidimetric method, and a sandwich enzyme immunoassay, and discloses that ELISA is most preferable. Examples described in the patent reference 2 do not include embodiments other than ELISA.

(non-patent reference 1) Biochemical and Biophysical Research Communications, (U.S.A.), 1996, vol. 221, p. 286-289

(non-patent reference 2) Gene, (Netherlands), 1997, vol. 190, p. 227-235

(non-patent reference 3) Hiroshi Hirose et al., No. 163, "Kessei adiponectin noudo to insulin teikousei: kenjyojin oyobi 2-gata tonyoubyou kanjya ni okeru kentou", "Meeting of the 75th Japanese endocrinology association study, Abstracts", The Japan Endocrine Society, 2002, p. 118

(non-patent reference 4) Yasuichi Ohmoto et al., "Adiponectin no ELISA kit ni tuite", Bio Clinica, 2002, vol. 17, p. 156-159

(non-patent reference 5) Yasuichi Ohmoto et al., "Adiponectin ELISA kit no kaihatsu to kecchu sonzai youshiki no kaiseki", Medical Science Digest, 2002, vol. 28, No. 12, p. 40-43

(non-patent reference 6) Arteriosclerosis, thrombosis, and vascular biology, (U.S.A.), 2003, vol. 23, p. 85-89

(non-patent reference 7) Circulation, (U.S.A.), 2003, vol. 107, p. 671-674

(non-patent reference 8) Journal of Biochemistry, 1996, vol. 120, p. 803-812

(patent reference 1) WO 99/21577

(patent reference 2) WO 03/016906

DISCLOSURE OF THE INVENTION

An object of the present invention is to remedy the above-mentioned disadvantages of the prior art, and to provide an analyzing reagent (particularly, an analyzing reagent for an automated analyzer) in which a predilution or pretreatment of a biological liquid (for example, blood, urine, cell cultures, tissue extracts, a cerebrospinal fluid, or secretory fluids, particularly blood) to be analyzed is not necessary, the analysis can be performed rapidly and conveniently, and facilities therefor are not limited.

As described above, the known ELISA methods need a pretreatment (for example, the heat treatment in the presence of SDS) of a sample, unless the monoclonal antibody having the special specificity (i.e., the monoclonal antibody which specifically reacts with a trimeric structure of adiponectin and/or a naturally-occurring adiponectin having a structure in which the trimers are further assembled) is used. Further, the known ELISA methods need a predilution of a sample. With the aim of developing a rapid and convenient adiponectin analyzing method without such a predilution or pretreatment, the present inventors have conducted intensive studies, and as a result, found that adiponectin can be analyzed without a pretreatment by using an anti-adiponectin polyclonal antibody in a latex agglutination method, instead of the ELISA methods. This method does not need a predilution of a sample, and exhibits an excellent correlation with the known ELISA method which needs the pretreatment (i.e., the heat treatment in the presence of SDS), as shown in EXAMPLES with experimental data.

In immunological analyzing methods, particularly recently, monoclonal antibodies are preferably used, because of an advantage in reproducibility as a reagent. Similarly, monoclonal antibodies are preferably used in latex agglutination methods. The tendency is supported by the patent references 1 and 2, that is, monoclonal antibodies are used in the ELISA methods disclosed in the patent references 1 and 2. In contradiction to the common approach, the present inventors used a polyclonal antibody, and unexpectedly found that the above object can be attained.

The above object can be solved by the present invention, i.e., a latex reagent for analyzing adiponectin, comprising a suspension of latex particles carrying a substance which specifically binds to adiponectin.

Further, the present invention relates to a method for analyzing adiponectin, comprising the steps of:

(1) obtaining a biological liquid possibly containing adiponectin, and (2) bringing the biological liquid, while maintaining the state in which the biological liquid is obtained, into contact with a suspension of latex particles carrying a substance which specifically binds to adiponectin, and optically analyzing a degree of latex-particles-agglutination.

BRIEF DESCRIPTION OF THE DRAWINGS

FIG. 1 is a graph showing the result obtained by measuring samples taken from healthy persons, using the latex reagent of the present invention for analyzing adiponectin.

BEST MODE FOR CARRYING OUT THE INVENTION

Figure 2:
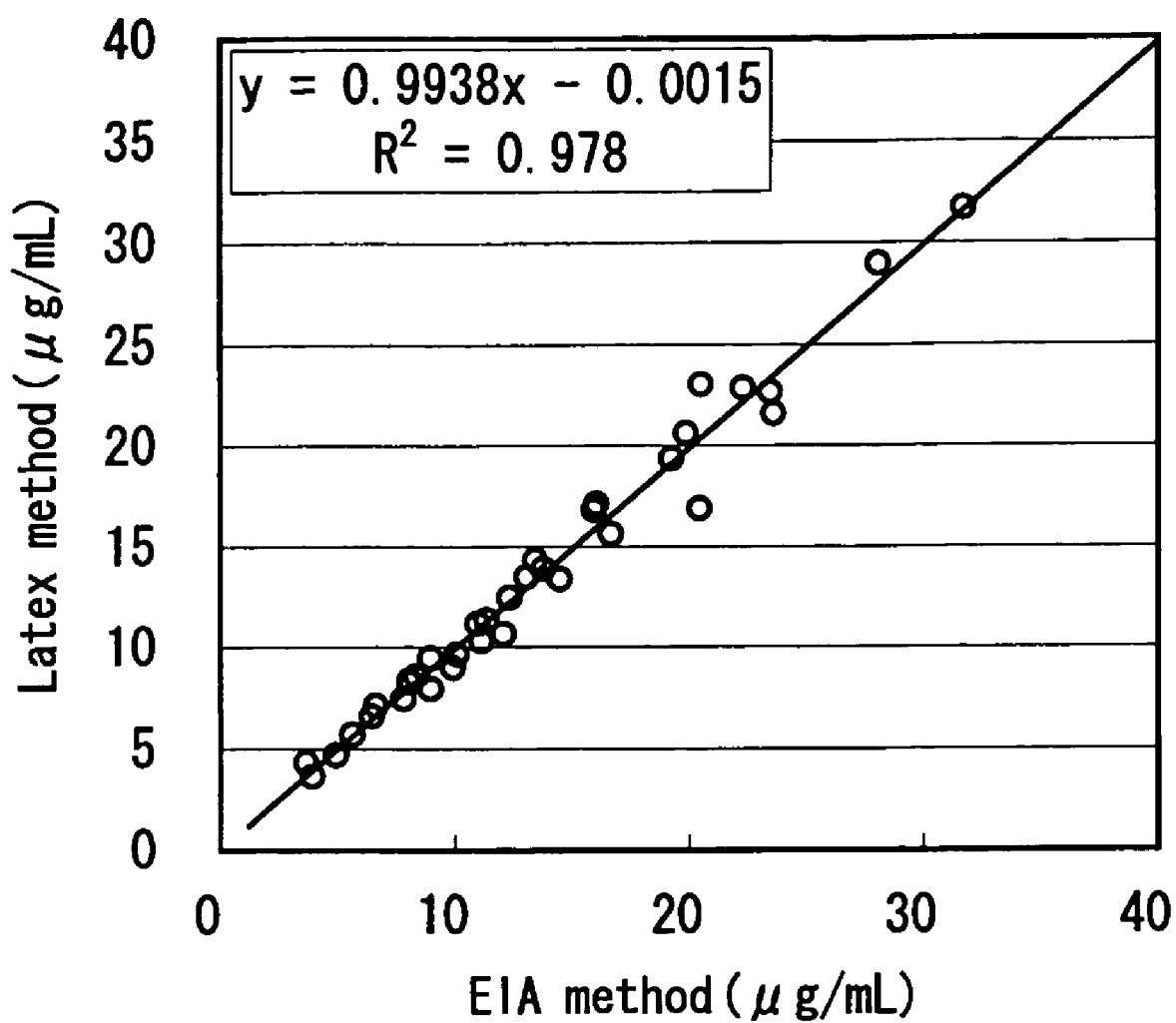
FIG. 2 is a graph showing a correlation between the latex reagent of the present invention for analyzing adiponectin and a conventional EIA method.

In the present invention, a latex agglutination reaction is utilized to analyze adiponectin. Adiponectin, a compound to be analyzed in the present invention, is a physiologically active substance secreted from adipose tissues. Adiponectin is a secretory protein composed of 244 amino acids, which was identified as a gene product of a gene apM1 (adipose most abundant gene transcript) specifically expressed in adipose tissues (Biochemical and Biophysical Research Communications, Vol. 221, p. 286-289, 1996; and Gene, Vol. 190, p. 227-235, 1997), and also called GBP28 (gelatin-binding protein of 28 kDa) (J. Biochem, vol. 120, p 803-812). Adiponectin is contained at a concentration of about 1 μg/mL to several tens of μg/mL in normal human blood. Although adiponectin is specifically secreted from adipocytes, obese persons show a significantly low concentration thereof in blood, and adiponectin is lowered in patients suffering from coronary diseases or type II diabetes, particularly diabetic macroangiopathy. Adiponectin may be regarded as a molecule involved in insulin resistance and arteriosclerosis. It is important in the prevention of coronary diseases to measure adiponectin rapidly and accurately.

A sample which can be analyzed by the present invention is not particularly limited, so long as it is a biological liquid which may contain adiponectin. As the sample, there may be mentioned, for example, a liquid directly taken from a living body [for example, blood (i.e., whole blood), urine, a cerebrospinal fluid, or secretory fluids], or a liquid obtained by treating biological materials such as organs, tissues, or cells taken from a living body [for example, extracts of organs, tissues, or cells, or cultures of tissues or cells].

Adiponectin is contained at a concentration of, for example, about 1 μg/mL to several tens of μg/mL (for example, 0.5 to 50 μg/mL, preferably 2 to 30 μg/mL, more preferably 5 to 15 μg/mL) in normal human blood.

Further, in a liquid derived from biological materials, which is generally prepared for a clinical laboratory test, adiponectin is contained at a concentration of about 1 μg/mL to several tens of μg/mL. Furthermore, an amount of a liquid for treating biological materials, such as a solution for extraction or a solution for culture, may be appropriately selected by a pilot test or the like, to adjust a concentration of adiponectin in the liquid derived from biological materials to about 1 μg/mL to several tens of μg/mL.

As above, a biological liquid (particularly blood) to be analyzed by the present invention may contain adiponectin at a concentration of about 1 μg/mL to several tens of μg/mL. Such a biological liquid may be analyzed, without predilution, by the latex reagent of the present invention for adiponectin analysis and the method of the present invention for adiponectin analysis.

As latex particles used in the present invention, there may be mentioned, for example, latex particles of polystyrene, or latex particles of styrene-styrene sulfate copolymer. An average particle size of latex particles carrying an adiponectin-binding substance may be appropriately selected within the range of 0.05 to 1.0 μm in accordance with, for example, a biological liquid to be analyzed, a concentration of adiponectin, or a measuring equipment.

When adiponectin in blood is analyzed, a normal human sample contains adiponectin at a high concentration of about 1 μg/mL to several tens of μg/mL, and a concentration thereof in blood is significantly lowered in an obese person. Accordingly, adiponectin in blood can be measured within a wide range by appropriately selecting a particle size of latex. For example, when the particle size is 0.1 μm or less, an accurate measurement may not always be ensured at a clinically useful concentration of 5 μg/mL or less. In contrast, when the particle size is 0.5 μm or more, a sample showing a normal high value may not always be measured. In the measuring system for adiponectin in blood, latex particles having an average particle size of 0.1 to 0.5 μm are preferable.

The adiponectin-binding substance used in the present invention is not particularly limited, so long as it specifically binds to adiponectin, and a latex agglutination reaction may be carried out when a biological liquid containing adiponectin is brought into contact with the adiponectin-binding substance carried on latex particles. As the specifically-binding substance, for example, an antibody such as a monoclonal antibody or a polyclonal antibody, or an aptamer (i.e., a functional RNA) which specifically binds to adiponectin may be used. As the antibody, for example, an immunoglobulin molecule per se, or an antibody fragment such as Fab, Fab', $F(ab')_2$, or Fv may be used.

When an antibody is used as the adiponectin-binding substance, an antibody prepared by using adiponectin or a derivative thereof (for example, a fragment of adiponectin, or a fused polypeptide containing adiponectin or a fragment thereof) as an immunogen, may be used. As the antibody, a polyclonal antibody prepared by using adiponectin or a derivative thereof as an immunogen, or a monoclonal antibody which recognizes an exposed epitope of adiponectin possibly contained in a sample is preferable. As the monoclonal antibody, a monoclonal antibody prepared by using a monomer of adiponectin as an immunogen, and recognizing an exposed epitope of adiponectin possibly contained in a sample is more preferable. In this connection, the adiponectin includes various forms of adiponectins, for example, a monomer thereof, a dimmer thereof, a trimmer thereof, or an aggregate thereof.

As the immunogen, for example, adiponectin or a derivative thereof prepared by genetic recombination techniques, or a naturally-occurring adiponectin may be used.

The antibody prepared by using as an immunogen adiponectin or a derivative thereof prepared by genetic recombination techniques may be prepared by, for example, a method described in WO99/21577. More particularly, an appropriate host such as E. coli, yeast, insect cells, or mammalian cells is used to express adiponectin or a derivative thereof. When E. coli is used as the host, adiponectin or a derivative thereof may be obtained as a soluble fraction, or inclusion bodies in the cell body. Adiponectin or a derivative thereof accumulated in the inclusion bodies may be solubilized with an appropriate denaturing agent such as guanidine hydrochloride or urea, and refolded to obtain adiponectin or a derivative thereof which may be used as the immunogen.

The antibody prepared by using as an immunogen a naturally-occurring adiponectin may be prepared by, for example, a method described in WO03/016906. More particularly, adiponectin which may be used as the immunogen can be prepared by utilizing a gelatin-binding activity of adiponectin, for example, by applying a large quantity of human plasma to a gelatin-immobilized column. As the naturally-occurring adiponectin possibly contained in a sample, there may be mentioned, for example, a monomer thereof, a dimmer thereof, a trimmer thereof, an aggregate thereof, or a globular region thereof generated by a protease digestion.

The polyclonal antibody may be obtained by immunizing an animal such as a rabbit with the prepared immunogen in accordance with an ordinary method. The monoclonal antibody may be obtained by using the prepared immunogen to prepare hybridomas.

Latex particles may be sensitized in accordance with an ordinary method. When an antibody is used as the adiponectin-binding substance, the sensitization may be carried out by physically or chemically binding the antibody to latex particles.

The form of the latex reagent of the present invention for analyzing adiponectin is not particularly limited, so long as it contains a suspension of latex particles carrying a substance which specifically binds to adiponectin. The latex reagent of the present invention may be, for example, a one-reagent-component system in which a buffer and the latex particles sensitized with the adiponectin-binding substance (for example, anti-adiponectin antibody) are contained in one reagent, or a two-reagent-components system (i.e., a kit composed of two reagents) in which the first reagent contains a buffer and the second reagent contains the latex particles sensitized with the adiponectin-binding substance (for example, antibody).

In the method of the present invention for analyzing adiponectin, a biological liquid possibly containing adiponectin is obtained, and then, the biological liquid without predilution and/or pretreatment (i.e., while maintaining the state in which the biological liquid is obtained) is brought into contact with a suspension of latex particles carrying a substance which specifically binds to adiponectin (preferably the latex reagent of the present invention for analyzing adiponectin).

For example, when an automated analyzer is used in the method of the present invention, after a biological liquid is obtained, predilution and/or pretreatment is not carried out before the biological liquid is applied in the automated analyzer. More particularly, after the biological liquid is obtained, the biological liquid without predilution and/or pretreatment (i.e., while maintaining the state in which the biological liquid is obtained) is brought into contact with a suspension of latex particles carrying a substance which specifically binds to adiponectin (preferably the latex reagent of the present invention for analyzing adiponectin) in the automated analyzer.

A preferred embodiment of the method of the present invention, using an automated analyzer, comprises the steps of:

(1) obtaining a biological liquid possibly containing adiponectin, and (2) bringing the biological liquid, while maintaining the state in which the biological liquid is obtained, into contact with a suspension of latex particles carrying a substance which specifically binds to adiponectin in an automated analyzer, and optically analyzing a degree of latex-particles-agglutination.

The term "predilution" as used herein means a dilution which is carried out after obtaining a biological liquid and before bringing the biological liquid into contact with the suspension of latex particles (preferably the latex reagent of the present invention for analyzing adiponectin). The predilution includes, for example, a dilution of a sample, generally required in a conventional immunological assay (for example, a radioimmunoassay or an enzyme immunoassay), such as a dilution step for solubilization.

The term "pretreatment" as used herein means various treatments which are carried out after obtaining a biological liquid and before bringing the biological liquid into contact with the suspension of latex particles (preferably the latex reagent of the present invention for analyzing adiponectin). The treatments include, for example, a physical or chemical separation of impurities from the biological liquid, and a chemical denaturing of the biological liquid [for example, a denaturing of a sample with a solubilizing agent or a detergent (for example, sodium dodecyl sulfate), required in an enzyme immunoassay].

In this connection, as the suspension of latex particles, when the latex reagent of the present invention consisting of the two-reagent-components system in which the first reagent contains a buffer and the second reagent contains the latex particles sensitized with the adiponectin-binding substance is used, a biological liquid is generally brought into contact with the first reagent, and the mixture is brought into contact with the second reagent. In this case, the biological liquid is diluted with the buffer as the first reagent. The dilution is an essential step for a 5-minute incubation in a general automated analyzer, and thus is not included in the above "predilution".

When a conventional radioimmunoassay or enzyme immunoassay is used in analyzing adiponectin contained in various biological liquids such as blood, a step of diluting a sample to, for example, 1/500 to 1/5000 is an essential step. Further, a step of treating a sample with a solubilizing agent or a detergent [for example, sodium dodecyl sulfate (SDS)] is an essential step in an enzyme immunoassay.

By contrast, in the method of the present invention for analyzing adiponectin, a latex agglutination reaction can be carried out by using an original biological liquid without predilution or pretreatment, for example, by appropriately selecting a particle size of the latex particle. When adiponectin in blood is analyzed, a particle size of 0.1 to 0.5 μm is preferable.

In the method of the present invention for analyzing adiponectin, latex particles carrying a substance which specifically bind to adiponectin (for example, the latex reagent of the present invention for analyzing adiponectin) are used to carry out an agglutination reaction, and a degree of the agglutination is optically analyzed (particularly measured) to analyze (particularly measure) an amount of adiponectin contained in a biological liquid such as blood. The optical analysis of a degree of the latex-particles-agglutination may be carried out by, for example, a visual observation, or an optical instrument for measuring an intensity of a scattered light, an absorbance, or an intensity of a transmitted light. A preferred measuring wavelength is 300 to 800 nm. The degree of agglutination may be carried out, in accordance with a known method, by selecting a size (average particle size) of the latex particle, a latex particle concentration, or a reaction time, and measuring an increase or decrease in an intensity of a scattered light, an absorbance, or an intensity of a transmitted light, or a combination thereof.

Generally, a concentration of latex particles sensitized with the adiponectin-binding substance, which is contained in a latex agglutination reaction system, may be appropriately selected in accordance with, for example, a concentration of coexistent additives such as salts, proteins, or saccharides. The concentration of latex particles (as the final concentration in a reaction system) may be preferably 0.05 to 10 mg/mL, more preferably 0.1 to 2 mg/mL. When the concentration of latex particles is too low, the agglutination reaction cannot always be measured accurately in a low concentration range, and thus the reproducibility is sometimes lowered. When the concentration is too high, the agglutination reaction cannot always be measured accurately in a high concentration range, and thus the reproducibility is sometimes lowered.

In the present invention, the latex-particles-agglutination reaction may be measured more accurately and a measurable range in a low concentration and a high concentration may be extended, by adjusting other factors which may affect the agglutination reaction of latex particles sensitized with the adiponectin-binding substance. As the factors, there may be mentioned, for example, a concentration of latex particles, an amount of an antibody sensitized on the latex particles, or a particle size of the latex particle.

The latex agglutination reaction in the method of the present invention for analyzing adiponectin may be carried out under the same conditions as those in a conventional latex agglutination reaction. As a reaction medium, various buffers may be appropriately selected in accordance with an adiponectin analysis in various biological liquids. When adiponectin in blood is analyzed, an ionic strength and a pH of the buffer are not particularly limited, so long as the buffer does not inactivate adiponectin in blood and does not inhibit the latex agglutination reaction. As the buffer, for example, a Good's buffer, a glycine buffer, or a tris buffer may be used. The pH in the reaction is preferably 5 to 10, more preferably 6 to 8. The reaction temperature is preferably 0 to 50° C., more particularly 20 to 40° C. The reaction time may be appropriately selected.

EXAMPLES

The present invention now will be further illustrated by, but is by no means limited to, the following Examples.

Example 1

Preparation of Reagent for Measuring Adiponectin (1) Preparation of Liquid of Latex Sensitized with Anti-Adiponectin Antibody An anti-human adiponectin polyclonal antibody derived from a rabbit was dissolved in a 0.01 mol/L tris buffer (pH 8.0) at a concentration of 0.5 mg/mL. To 9 mL of the polyclonal antibody solution, 1 mL of a polystyrene latex solution (average particle size=0.2 μm, solid content=10% by weight) was added, and the mixture was stirred at room temperature for 60 minutes. A tris buffer (pH 8.0) containing 0.5% by weight of bovine serum albumin was added to the mixture. The whole was stirred at room temperature for 60 minutes, and centrifuged at 20000 rpm. The resulting precipitate, i.e., latex, was suspended in 10 mL of a tris buffer (pH 8.0) to prepare a liquid of latex sensitized with the anti-adiponectin antibody.

In this connection, the above polyclonal antibody was prepared by the method described in Example 1 of WO99/21577. That is, it was a polyclonal antibody obtained by using as an immunogen adiponectin prepared by genetic recombination techniques.

In this example, three liquids (lot Nos. 01 to 03) of latex sensitized with the anti-adiponectin antibody were prepared in accordance with the above-mentioned procedure, and evaluated in the following Example 2.

(2) Preparation of Buffer

Sodium chloride was added at a concentration of 0.9% by weight to a 0.1 mol/L tris buffer (pH8.0) containing 0.5% by weight of bovine serum albumin, to prepare a buffer.

(3) Reagent for Measuring Human Adiponectin Antigen

A reagent, used in this example, for measuring a human adiponectin antigen was constructed as a two-reagent-components system composed of the buffer prepared in Example 1(2) as the first reagent, and the latex sensitized with the anti-adiponectin antibody prepared in Example 1(1) as the second reagent.

(4) Standard Adiponectin Antigen Liquids

A serum containing adiponectin at a high concentration, which was collected from a non-obese subject, was diluted with a physiological saline to prepare standard adiponectin antigen liquids containing known concentrations of adiponectin.

Example 2

Measurement of Adiponectin in Blood (1) Measurement of Adiponectin in Blood

To 2 μL of each sample to be measured (blood collected from a thin subject), 90 μL of the buffer prepared in Example 1(2) was added, and the mixture was allowed to stand at 37° C. To the mixture, 90 μL of the liquid of latex sensitized with the anti-adiponectin antibody prepared in Example 1(1) was added and stirred. From the last addition, an absorbance at the wavelength of 570 nm was measured for 5 minutes. An amount of change in absorbance therebetween was regarded as an amount of change in absorbance (ΔAbs). A calibration curve was prepared on the basis of each ΔAbs of the standard adiponectin antigen liquids and the concentration thereof. The calibration curve was used to calculate an amount of adiponectin from the ΔAbs of each sample. The measurement was carried out using an automated analyzer (Hitachi 7170, Hitachi Ltd.).

The result is shown in Table 1 and FIG. 1. As shown in Table 1 and FIG. 1, it was confirmed that the sensitized latex liquids lot Nos. 01 to 03 may be used to measure adiponectin from a low concentration to a high concentration with respect to theoretical values of diluted adiponectin.

TABLE 1

| Lot of reagent (a) μg/mL | Lot 01 (b) Abs × 10⁴ | Lot 02 (b) Abs × 10⁴ | Lot 03 (b) Abs × 10⁴ |
|---|---|---|---|
| 0.00 | −3 | −2 | −2 |
| 0.20 | 13 | 10 | 12 |
| 0.39 | 26 | 25 | 28 |
| 0.79 | 52 | 52 | 54 |

TABLE 1-continued

| Lot of reagent (a) μg/mL | Lot 01 (b) Abs × 10⁴ | Lot 02 (b) Abs × 10⁴ | Lot 03 (b) Abs × 10⁴ |
|---|---|---|---|
| 1.18 | 81 | 78 | 82 |
| 1.57 | 108 | 106 | 110 |
| 1.97 | 135 | 133 | 138 |
| 2.36 | 162 | 164 | 164 |
| 2.75 | 191 | 188 | 196 |
| 3.14 | 220 | 215 | 220 |
| 3.54 | 248 | 245 | 254 |
| 3.93 | 275 | 273 | 284 |
| 7.86 | 570 | 567 | 582 |
| 11.79 | 860 | 844 | 877 |
| 15.72 | 1161 | 1140 | 1182 |
| 19.65 | 1443 | 1415 | 1456 |
| 23.58 | 1707 | 1680 | 1722 |
| 27.51 | 1947 | 1895 | 1982 |
| 31.44 | 2164 | 2110 | 2201 |
| 35.37 | 2342 | 2311 | 2405 |
| 39.30 | 2497 | 2486 | 2562 |
| 47.16 | 2679 | 2626 | 2724 |
| 70.74 | 3071 | 2990 | 3115 |
| 94.32 | 3134 | 3052 | 3189 |
| 117.90 | 3042 | 2968 | 3138 |

[(a): Theoretical value of diluted adiponectin; and (b): Sensitivity]

(2) Determination of Minimum Detectable Sensitivity (Low Detection Limit)

The procedure described in Example 2(1) was repeated except that samples to be measured were collected from healthy persons.

The result is shown in Table 2. In Table 2, "N", "MAX", "MIN", "RANGE", "MEAN", "SD", and "CV" mean "number of subjects to be measured", "maximum value", "minimum value", "difference between the maximum value and the minimum value", "mean value", "standard deviation", and "coefficient of variation", respectively.

As shown in Table 2, it was confirmed that a concentration in which the "MEAN+2SD" value of ΔAbs (0 μg/mL) did not overlap with the "MEAN−2SD" value was 0.1 μg/mL.

TABLE 2

| | 0 μg/mL | 0.1 μg/mL | 0.2 μg/mL | 0.3 μg/mL | 0.4 μg/mL | 0.5 μg/mL | 0.6 μg/mL | 0.7 μg/mL | 0.8 μg/mL | 0.9 μg/mL | 1 μg/mL |
|---|---|---|---|---|---|---|---|---|---|---|---|
| 1 | 0.000 | 0.061 | 0.253 | 0.314 | 0.406 | 0.429 | 0.566 | 0.620 | 0.834 | 0.933 | 0.948 |
| 2 | 0.000 | 0.038 | 0.161 | 0.337 | 0.436 | 0.505 | 0.543 | 0.650 | 0.826 | 0.750 | 1.016 |
| 3 | 0.000 | 0.092 | 0.260 | 0.299 | 0.444 | 0.513 | 0.574 | 0.673 | 0.826 | 0.902 | 1.032 |
| 4 | 0.000 | 0.061 | 0.184 | 0.322 | 0.375 | 0.444 | 0.605 | 0.704 | 0.742 | 0.902 | 1.085 |
| 5 | 0.000 | 0.077 | 0.237 | 0.329 | 0.329 | 0.513 | 0.528 | 0.704 | 0.773 | 0.895 | 1.032 |
| 6 | 0.000 | 0.100 | 0.253 | 0.360 | 0.375 | 0.482 | 0.582 | 0.658 | 0.811 | 0.895 | 1.032 |
| 7 | 0.008 | 0.100 | 0.222 | 0.314 | 0.436 | 0.505 | 0.536 | 0.696 | 0.795 | 0.955 | 0.971 |
| 8 | 0.000 | 0.107 | 0.191 | 0.337 | 0.398 | 0.498 | 0.566 | 0.681 | 0.818 | 0.917 | 0.986 |
| 9 | 0.000 | 0.061 | 0.138 | 0.314 | 0.436 | 0.482 | 0.612 | 0.643 | 0.818 | 0.910 | 1.039 |
| 10 | 0.000 | 0.123 | 0.207 | 0.276 | 0.360 | 0.498 | 0.566 | 0.696 | 0.826 | 0.948 | 1.001 |
| N | 10 | 10 | 10 | 10 | 10 | 10 | 10 | 10 | 10 | 10 | 10 |
| MAX | 0.008 | 0.123 | 0.260 | 0.360 | 0.444 | 0.513 | 0.612 | 0.704 | 0.834 | 0.955 | 1.085 |
| MIN | 0.000 | 0.038 | 0.138 | 0.276 | 0.329 | 0.429 | 0.528 | 0.620 | 0.742 | 0.750 | 0.948 |
| RANGE | 0.008 | 0.085 | 0.122 | 0.084 | 0.115 | 0.084 | 0.084 | 0.084 | 0.092 | 0.205 | 0.137 |
| MEAN | 0.001 | 0.082 | 0.211 | 0.320 | 0.399 | 0.487 | 0.568 | 0.672 | 0.807 | 0.901 | 1.014 |
| SD | 0.003 | 0.027 | 0.042 | 0.023 | 0.039 | 0.029 | 0.027 | 0.029 | 0.029 | 0.057 | 0.039 |
| CV | 316.23% | 32.36% | 19.83% | 7.17% | 9.78% | 5.93% | 4.84% | 4.29% | 3.60% | 6.34% | 3.86% |
| MEAN − 2SD | — | 0.03 | 0.13 | 0.27 | 0.32 | 0.43 | 0.51 | 0.61 | 0.75 | 0.79 | 0.94 |
| MEAN + 2SD | 0.01 | — | — | — | — | — | — | — | — | — | — |

(3) Confirmation of Correlation with EIA Method

As the latex method of the present invention, the procedure described in Example 2(1) was repeated except that samples to be measured were collected from healthy persons.

An EIA method was carried out using a commercially available laboratory reagent (Human adiponectin ELISA kit; Otsuka Pharmaceutical). The ELISA reagent is a commercially available reagent on the basis of an ELISA method described in WO99/21577. In the ELISA reagent, a combination of a monoclonal antibody and a polyclonal antibody prepared by using as an immunogen adiponectin prepared by genetic recombination techniques is used as anti-adiponectin antibodies, and a pretreatment (a heat treatment in the presence of SDS) of a sample and a dilution step are essential steps.

The result is shown in FIG. 2. As shown in FIG. 2, the correlation between the latex method of the present invention and the EIA method using the commercially available laboratory reagent was shown as the following equation:

$$Y = 0.9938x - 0.0015 \ (R=0.9889)$$

and a high correlation was confirmed.

(4) Confirmation of Effects of Impurities

The procedure described in Example 2(1) was repeated except that samples prepared by adding various impurities (bilirubin F, bilirubin C, hemoglobin, formazin turbidity, intrafat, or rheumatoid factor) at desired concentrations to samples taken from healthy persons were used as samples to be measured.

The results are shown in Table 3 to Table 14. It was confirmed that the effect of each impurity [bilirubin F, bilirubin C, hemoglobin, formazin turbidity, intrafat, or rheumatoid factor (RF)] at each concentration was within ±10%.

TABLE 3

| | | sample 1 | |
|---|---|---|---|
| bilirubin F | (a) (mg/dL) | (b) (μg/mL) | (C) (%) |
| 0/5 | 0.0 | 2.14 | 100.0% |
| 1/5 | 6.0 | 2.10 | 98.0% |
| 2/5 | 12.0 | 2.09 | 97.5% |
| 3/5 | 18.0 | 2.09 | 97.5% |
| 4/5 | 24.0 | 2.09 | 97.5% |
| 5/5 | 30.0 | 2.06 | 96.3% |

[(a): Concentration added, (b): Measured value, and (C): Rate of recover; in Tables 3 to 14]

TABLE 4

| | | sample 2 | |
|---|---|---|---|
| bilirubin F | (a) (mg/dL) | (b) (μg/mL) | (C) (%) |
| 0/5 | 0.0 | 6.45 | 100.0% |
| 1/5 | 6.0 | 6.45 | 100.1% |
| 2/5 | 12.0 | 6.42 | 99.5% |
| 3/5 | 18.0 | 6.41 | 99.3% |
| 4/5 | 24.0 | 6.43 | 99.6% |
| 5/5 | 30.0 | 6.44 | 99.8% |

TABLE 5

| | | sample 1 | |
|---|---|---|---|
| bilirubin C | (a) (mg/dL) | (b) (μg/mL) | (C) (%) |
| 0/5 | 0.0 | 2.07 | 100.0% |
| 1/5 | 6.0 | 2.05 | 99.2% |
| 2/5 | 12.0 | 2.08 | 100.5% |
| 3/5 | 18.0 | 2.05 | 99.2% |
| 4/5 | 24.0 | 2.06 | 99.7% |
| 5/5 | 30.0 | 2.08 | 100.6% |

TABLE 6

| | | sample 2 | |
|---|---|---|---|
| bilirubin C | (a) (mg/dL) | (b) (μg/mL) | (C) (%) |
| 0/5 | 0.0 | 6.41 | 100.0% |
| 1/5 | 6.0 | 6.41 | 100.0% |
| 2/5 | 12.0 | 6.43 | 100.3% |
| 3/5 | 18.0 | 6.45 | 100.6% |
| 4/5 | 24.0 | 6.41 | 99.9% |
| 5/5 | 30.0 | 6.37 | 99.4% |

TABLE 7

| | | sample 1 | |
|---|---|---|---|
| hemoglobin | (a) (mg/dL) | (b) (μg/mL) | (C) (%) |
| 0/5 | 0.0 | 2.06 | 100.0% |
| 1/5 | 100.0 | 2.06 | 100.0% |
| 2/5 | 200.0 | 2.04 | 99.2% |
| 3/5 | 300.0 | 2.06 | 100.3% |
| 4/5 | 400.0 | 2.08 | 101.1% |
| 5/5 | 500.0 | 2.06 | 100.2% |

TABLE 8

| | | sample 2 | |
|---|---|---|---|
| hemoglobin | (a) (mg/dL) | (b) (μg/mL) | (C) (%) |
| 0/5 | 0.0 | 6.40 | 100.0% |
| 1/5 | 100.0 | 6.43 | 100.5% |
| 2/5 | 200.0 | 6.26 | 97.9% |
| 3/5 | 300.0 | 6.38 | 99.7% |
| 4/5 | 400.0 | 6.39 | 99.8% |
| 5/5 | 500.0 | 6.41 | 100.3% |

TABLE 9

| | | sample 1 | |
|---|---|---|---|
| formazin turbidity | (a) (turbidity) | (b) (μg/mL) | (C) (%) |
| 0/5 | 0.0 | 2.12 | 100.0% |
| 1/5 | 400.0 | 2.13 | 100.5% |
| 2/5 | 800.0 | 2.07 | 97.8% |
| 3/5 | 1200.0 | 2.06 | 97.0% |
| 4/5 | 1600.0 | 2.11 | 99.7% |
| 5/5 | 2000.0 | 2.07 | 97.6% |

TABLE 10

|  | sample 2 | | |
|---|---|---|---|
| formazin Turbidity | (a) (turbidity) | (b) (μg/mL) | (C) (%) |
| 0/5 | 0.0 | 6.38 | 100.0% |
| 1/5 | 400.0 | 6.37 | 99.8% |
| 2/5 | 800.0 | 6.34 | 99.4% |
| 3/5 | 1200.0 | 6.35 | 99.4% |
| 4/5 | 1600.0 | 6.38 | 99.9% |
| 5/5 | 2000.0 | 6.44 | 100.9% |

TABLE 11

|  | sample 1 | | |
|---|---|---|---|
| intrafat | (a) (%) | (b) (μg/mL) | (C) (%) |
| 0/5 | 0.0 | 2.10 | 100.0% |
| 1/5 | 1.0 | 2.12 | 100.8% |
| 2/5 | 2.0 | 2.10 | 100.0% |
| 3/5 | 3.0 | 2.14 | 101.9% |
| 4/5 | 4.0 | 2.15 | 102.2% |
| 5/5 | 5.0 | 2.13 | 101.3% |

TABLE 12

|  | sample 2 | | |
|---|---|---|---|
| intrafat | (a) (%) | (b) (μg/mL) | (C) (%) |
| 0/5 | 0.0 | 6.42 | 100.0% |
| 1/5 | 1.0 | 6.42 | 100.0% |
| 2/5 | 2.0 | 6.44 | 100.3% |
| 3/5 | 3.0 | 6.34 | 98.7% |
| 4/5 | 4.0 | 6.32 | 98.4% |
| 5/5 | 5.0 | 6.31 | 98.2% |

TABLE 13

|  | sample 1 | | |
|---|---|---|---|
| RF | (a) (IU/mL) | (b) (μg/mL) | (C) (%) |
| 0/5 | 0.0 | 2.10 | 100.0% |
| 1/5 | 50.0 | 2.06 | 98.1% |
| 2/5 | 100.0 | 2.05 | 97.3% |
| 3/5 | 150.0 | 2.10 | 100.0% |
| 4/5 | 200.0 | 2.03 | 96.7% |
| 5/5 | 250.0 | 2.12 | 100.6% |

TABLE 14

|  | sample 2 | | |
|---|---|---|---|
| RF | (a) (IU/mL) | (b) (μg/mL) | (C) (%) |
| 0/5 | 0.0 | 6.42 | 100.0% |
| 1/5 | 50.0 | 6.30 | 98.2% |
| 2/5 | 100.0 | 6.39 | 99.6% |
| 3/5 | 150.0 | 6.27 | 97.8% |
| 4/5 | 200.0 | 6.30 | 98.2% |
| 5/5 | 250.0 | 6.42 | 100.1% |

INDUSTRIAL APPLICABILITY

According to the present invention, in the analysis for adiponectin contained in a biological liquid (preferably blood) on the basis of a latex agglutination reaction using latex particles, the measurable range can be extended from a low concentration to a high concentration without a pretreatment or predilution of a sample. Further, the analysis of the present invention can be performed rapidly and conveniently, and facilities therefor are not limited.

An automated analyzer able to handle many samples in a short time is now widely used, and a high-sensitivity is desired. Accordingly, a latex agglutination method making use of the reaction with a latex particle carrying an antibody (or an antigen) is widely used. The analysis of the present invention does not need a pretreatment and/or predilution, and thus, the analysis can be performed in a short time (for example, approximately 10 to 15 minutes). The latex reagent of the present invention for analyzing adiponectin (preferably adiponectin in blood) is suitable for an analyzing reagent for an automated analyzer.

Although the present invention has been described with reference to specific embodiments, various changes and modifications obvious to those skilled in the art are possible without departing from the scope of the appended claims.

The invention claimed is:

1. A latex reagent for quantitatively measuring adiponectin, comprising a suspension of latex particles carrying an anti-adiponectin polyclonal antibody that binds to native adiponectin.

2. The latex reagent according to claim 1, wherein the latex particles do not carry an anti-adiponectin monoclonal antibody.

3. A method for quantitatively measuring native adiponectin, comprising the steps of:
    (1) obtaining a biological liquid possibly containing adiponectin, and
    (2) bringing the biological liquid, without pretreatment of said liquid to obtain monomeric adiponectin or predilution, into contact with a suspension of latex particles carrying an anti-adiponectin polyclonal antibody that binds to native adiponectin, and optically analyzing a degree of latex-particles-agglutination, wherein said degree of latex-particle agglutination correlates to the level of adiponectin in said liquid.

4. The method according to claim 3, wherein the latex particles do not carry an anti-adiponectin monoclonal antibody.

5. A method for quantitatively measuring the level of native adiponectin in a biological liquid, consisting of the steps of:
    (1) obtaining a biological liquid possibly containing adiponectin; and
    (2) bringing the biological liquid, without predilution or other pretreatment, into contact with a suspension of latex particles carrying an anti-adiponectin polyclonal antibody that binds to native adiponectin, and optically analyzing a degree of latex-particle-agglutination, wherein said degree of latex-particle agglutination correlates to the level of adiponectin in said liquid.

* * * * *

UNITED STATES PATENT AND TRADEMARK OFFICE
CERTIFICATE OF CORRECTION

PATENT NO. : 7,659,125 B2 Page 1 of 1
APPLICATION NO. : 10/550324
DATED : February 9, 2010
INVENTOR(S) : Tachikawa et al.

It is certified that error appears in the above-identified patent and that said Letters Patent is hereby corrected as shown below:

On the title page item (73): Delete "Latron" and insert --Iatron--

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,659,125 B2  Page 1 of 1
APPLICATION NO. : 10/550324
DATED : February 9, 2010
INVENTOR(S) : Tachikawa et al.

It is certified that error appears in the above-identified patent and that said Letters Patent is hereby corrected as shown below:

On the title page item (73), should read: -- Mitsubishi Kagaku Iatron, Inc., Tokyo, (JP) and Otsuka Pharmaceutical Co., Ltd., Tokyo (JP) --

Signed and Sealed this

Seventh Day of September, 2010

David J. Kappos
*Director of the United States Patent and Trademark Office*